United States Patent
Wang et al.

(10) Patent No.: US 12,133,847 B2
(45) Date of Patent: Nov. 5, 2024

(54) PHARMACEUTICAL COMPOSITION AND PREPARATION METHOD THEREFOR

(71) Applicant: Shenzhen Pharmacin Co., Ltd., Guangdong (CN)

(72) Inventors: Zeren Wang, Yunnan (CN); Yulan Zhao, Yunnan (CN); Lijiang Wang, Yunnan (CN); Xiao Zhang, Yunnan (CN); Jun Xu, Shenzhen (CN); Shunqin Chen, Shenzhen (CN); Meili Sun, Shenzhen (CN); Guisheng Jiang, Shenzhen (CN)

(73) Assignee: Shenzhen Pharmacin, Co., Ltd., Shenzhen (CN)

( * ) Notice: Subject to any disclaimer, the term of this patent is extended or adjusted under 35 U.S.C. 154(b) by 313 days.

(21) Appl. No.: 17/369,531

(22) Filed: Jul. 7, 2021

(65) Prior Publication Data

US 2021/0401819 A1  Dec. 30, 2021

Related U.S. Application Data

(60) Continuation of application No. 16/727,469, filed on Dec. 26, 2019, now Pat. No. 11,083,721, which is a division of application No. 16/156,983, filed on Oct. 10, 2018, now Pat. No. 10,864,204, which is a continuation of application No. 15/636,353, filed on Jun. 28, 2017, now Pat. No. 10,159,664, which is a continuation of application No. PCT/CN2015/100263, filed on Dec. 31, 2015.

(30) Foreign Application Priority Data

Dec. 31, 2014 (CN) .......................... 201410853865.2
Dec. 25, 2015 (CN) .......................... 201510988362.0

(51) Int. Cl.
| | |
|---|---|
| A61K 31/4439 | (2006.01) |
| A61K 9/48 | (2006.01) |
| A61K 47/02 | (2006.01) |
| A61K 47/12 | (2006.01) |
| A61K 47/18 | (2017.01) |

(52) U.S. Cl.
CPC ........ *A61K 31/4439* (2013.01); *A61K 9/4858* (2013.01); *A61K 47/02* (2013.01); *A61K 47/12* (2013.01); *A61K 47/183* (2013.01)

(58) Field of Classification Search
CPC ... A61K 31/4439; A61K 9/4858; A61K 47/02
See application file for complete search history.

(56) References Cited

U.S. PATENT DOCUMENTS

| | | | |
|---|---|---|---|
| 3,663,271 A | 5/1972 | Gerhard | |
| 4,678,661 A | 7/1987 | Gergely et al. | |
| 5,503,846 A | 4/1996 | Wehling et al. | |
| 6,087,380 A | 7/2000 | Hauel et al. | |
| 7,208,489 B2 | 4/2007 | Barvian et al. | |
| 7,456,168 B2 | 11/2008 | Barvian et al. | |
| 7,866,474 B2 | 1/2011 | Geser et al. | |
| 7,932,273 B2 | 4/2011 | Schmid et al. | |
| 9,034,822 B2 | 5/2015 | Van Ryn et al. | |
| 9,925,174 B2 | 3/2018 | Brauns et al. | |
| 10,159,664 B2 | 12/2018 | Shenzhen | |
| 11,083,721 B2 * | 8/2021 | Wang ...................... A61P 43/00 | |
| 2005/0038077 A1 | 2/2005 | Kohlrausch | |

FOREIGN PATENT DOCUMENTS

| | | |
|---|---|---|
| CN | 1638771 A | 7/2005 |
| CN | 1775289 A | 5/2006 |
| CN | 104224754 A | 12/2014 |
| CN | 105797162 A | 7/2016 |
| CN | 106924256 A | 7/2017 |
| EP | 0962443 B1 | 4/2003 |
| EP | 3251672 A1 | 12/2017 |
| JP | 2009173615 A | 8/2009 |
| WO | WO-9421239 A1 | 9/1994 |
| WO | WO-03074056 A1 | 9/2003 |
| WO | WO-2013124340 A1 | 8/2013 |

OTHER PUBLICATIONS

Decision to Grant JP Appl. No. 2017-535819, mailed Jul. 30, 2019.
EP Search Report for EP15875281.6 dated Jul. 9, 2018.
European Application No. 15875281.6 Extended European Search Report Mailed Jul. 9, 2018.
Ibrance Drug Label Feb. 2018.
Non-Final Office Action dated Aug. 6, 2019 for U.S. Appl. No. 16/156,983.
Non-Final Office Action dated Jun. 24, 2020 for U.S. Appl. No. 16/727,469.
Office Action Japanese Application No. 2017-535819 Mailed Apr. 17, 2018.
Pradaxa Drug Label—Revised Mar. 2018; 27 pages.
Shuangping, Yu et al., Progress in Surface Modification of Superfine Powder, Journal of Guangdong University of Technology, Jun. 30, 2003, pp. 70-76.

(Continued)

*Primary Examiner* — Kevin E Weddington
(74) *Attorney, Agent, or Firm* — Wilson Sonsini Goodrich & Rosati

(57) ABSTRACT

The present invention provides an oral pharmaceutical composition and a usage thereof, comprising a pharmaceutically acceptable acidic medicinal auxiliary material whose surface is modified and dabigatran etexilate or pharmaceutically acceptable salts or aquo-complexes thereof. The present invention further provides a surface modification method for a medicinal auxiliary material.

21 Claims, 2 Drawing Sheets

(56) References Cited

OTHER PUBLICATIONS

Suleimen, S. et al., "Kinetics of the acid-catalyzed hydrolysis of famotidine," International Journal of Pharmaceutics, 1989;54(1):65-69.

* cited by examiner

PHARMACEUTICAL COMPOSITION AND PREPARATION METHOD THEREFOR

CROSS-REFERENCE

This application is a Continuation of U.S. patent application Ser. No. 16/727,469, filed Dec. 26, 2019, U.S. Pat. No. 11,083,721, issued Aug. 10, 2021, which is a division of Ser. No. 16/156,983, filed Oct. 10, 2018, U.S. Pat. No. 10,864,204, issued Dec. 15, 2020 which is a Continuation of U.S. patent application Ser. No. 15/636,353, filed Jun. 28, 2017, U.S. Pat. No. 10,159,664, issued Dec. 25, 2018 which is a Continuation of U.S. International Patent Application No. PCT/CN2015/100263, filed Dec. 31, 2015, which claims the benefit of International Patent Application No. CN201410853865.2, filed Dec. 31, 2014, and International Patent Application No. CN201510988362.0, filed on Dec. 25, 2015, each of which is incorporated herein by reference in its entirety.

TECHNICAL FIELD

The present invention relates to a pharmaceutical composition comprising a pharmaceutically acceptable surface-modified acidic medicinal auxiliary material. In particular, the present invention relates to a pharmaceutical composition comprising dabigatran etexilate (an active substance) or a pharmaceutically acceptable salt or hydrate thereof and a pharmaceutically acceptable surface-modified acidic medicinal auxiliary material. The present invention also relates to the field of surface modification of a medicinal auxiliary material, and in particular, to a method for surface modification of a medicinal auxiliary material.

BACKGROUND ART

Many drugs will undergo a chemical reaction in the present of acidic or alkaline materials, resulting in a chemical degradation of the drugs. In general, the use of acidic or alkaline materials should be avoided in the formulation products of drugs which decompose in the present of acids or alkalis. However, in some special cases, some acidic or alkaline materials may be needed for such unstable drugs, so as to enable the formulation products of these drugs to meet certain requirements.

Dabigatran etexilate is one of those drugs, which has the chemical structure of ethyl 3-[(2-{4-(hexyloxycarbonylamino-imino-methyl)-phenylamino]-methyl}-1-methyl-1H-benzimidazole-5-carbonyl)-pyridin-2-yl-amino]-propionate, and the molecular formula of this compound is represented by the following formula (I):

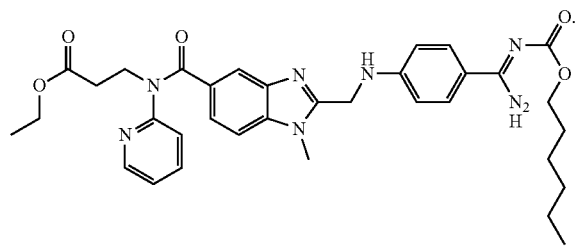

Formula (I)

Dabigatran etexilate was developed by Germany Boehringer Ingelheim Company, and had first entered into market in Germany and the UK in April 2008 and then was approved for marketing in American on Oct. 19, 2010. The trade name in English of this drug is Pradaxa, and the general name in English of this drug is dabigatran etexilate mesylate. The general name in Chinese of this drug is "甲磺酸达比加群酯".

This molecule is a binary prodrug. Esters are formed at both ends of the molecule. After entering into the body, the esters at both ends will undergo an enzymatic hydrolysis to form a dibasic acid, namely dabigatran, which is the exactly active pharmaceutical molecule. However, the structure of the dabigatran molecule is too polar to penetrate the intestinal wall cells, resulting in a very low oral bioavailability, and it can only penetrate the intestinal wall cells and be orally administrated after it is esterified.

As a prodrug of dabigatran, dabigatran etexilate is a novel and the only oral type of direct thrombin inhibitor, and belongs to a nonpeptidic thrombin inhibitor. Upon gastrointestinal absorption after oral administration, it is conversed in vivo to dabigatran having a direct anticoagulant activity. By binding to fibrin-specific binding sites of thrombin, dabigatran prevents the cleavage of fibrinogen into fibrin, thereby blocking the final step of the coagulation cascade network and thrombosis. Dabigatran can be dissociated from the fibrin-thrombin complex and play a reversible anticoagulant effect. As compared with the targets of other anticoagulants and platelet inhibitors in the prior art, the target of this drug is closer to the end of the reaction cascade, and thus this drug has a more definite mechanism of action and a better selectivity.

Dabigatran etexilate has a poor solubility, and in order to increase its solubility, it is developed as a formulation and used clinically in the form of salt (dabigatran etexilate mesylate). The solubility of dabigatran etexilate mesylate is strongly dependent on pH. Dabigatran etexilate mesylate has a high solubility in acidic media and a very poor solubility in neutral and alkaline media and is substantially insoluble in physiological conditions, namely, in the intestine near pH 7.0, resulting in a poor bioavailability.

Due to these physicochemical and biopharmaceutical properties of dabigatran etexilate mesylate, some efforts have been made to obtain a stable dabigatran etexilate mesylate composition exhibiting the desired bioavailability.

Chinese Patent No. ZL03805473.6 discloses a formulation and process characterized by coating an insulating layer and an active substance (comprising dabigatran etexilate or a pharmaceutically acceptable salt thereof, preferably dabigatran etexilate mesylate) layer on a substantially spherical acid core material which consists of or contains a pharmaceutically acceptable organic acid, wherein the organic acid contained in the acid core material has a solubility of greater than 1 g/250 ml in water at 20° C., and the organic acid core material and the active substance layer are separated from each another by the insulating layer. The formulation (containing an organic acid) prepared by this process has a significantly improved bioavailability as compared with conventional formulations (free of an organic acid), because the organic acid added into conventional formulations may produce in the aqueous solution of the gastrointestinal tract an acid microenvironment (also called as acid microclimate) in which dabigatran etexilate mesylate can dissolve, enabling dabigatran etexilate mesylate to be absorbed in vivo after being dissolved.

As mentioned in this patent, dabigatran etexilate mesylate is extremely liable to acids, but it is necessary to add an organic acid to the formulation product in order to improve the bioavailability of the formulation product. In this patent, a high molecular weight polymer is used to coat the outer surface of pellets with a film so as to form an insulating layer, and then the outer surface of the insulating layer is coated with dabigatran etexilate mesylate. The process comprises loading the drug in a fluidized state onto the surface of the organic acid core material, that is, the drug is formulated into a suspension for loading. Accordingly, the process has the disadvantages of a low drug loading rate, a great loss of drug, unevenness of drug loading, an uncertain amount of the drug loaded, complex operations and the like. Further, the spherical degree of the prepared organic acid pellet core, the perfection degree of the insulating layer coating, the combination degree of the active substance and the insulating layer etc. need to be strictly controlled, resulting in high production costs and a long production period.

SUMMARY OF INVENTION

The present invention has been made in view of the above-mentioned problems in the prior art, and an object of the present invention is to provide an oral pharmaceutical composition of dabigatran etexilate or a salt or hydrate thereof, comprising a pharmaceutically acceptable surface-modified acidic medicinal auxiliary material. The pharmaceutical composition is chemically stable, exhibits a high solubility, and provides the desired bioavailability. Meanwhile, the pharmaceutical composition has a simple preparation process and low production costs, which solves many problems in the prior art process. The pharmaceutically acceptable surface-modified acidic medicinal auxiliary material of the present invention may be also applicable to other pharmaceutical compositions which are labile to acids or alkalis in the formulation that however requires the use of acidic auxiliary materials or alkaline auxiliary materials therein.

Specifically, the present invention provides a pharmaceutically acceptable surface-modified acidic medicinal auxiliary material or alkaline medicinal auxiliary material that is applicable to pharmaceutical compositions which are labile to acids or alkalis in the formulation that however requires the use of acidic medicinal auxiliary materials or alkaline medicinal auxiliary materials therein.

More specifically, the present invention provides an oral pharmaceutical composition comprising: a) a pharmaceutically acceptable surface-modified acidic medicinal auxiliary material, b) ethyl 3-[(2-{4-(hexyloxycarbonylamino-imino-methyl)-phenylamino]-methyl}-1-methyl-1H-benzimidazole-5-carbonyl)-pyridin-2-yl-amino]-propionate that is also called as dabigatran etexilate, or a pharmaceutically acceptable salt or hydrate thereof.

Preferably, the pharmaceutically acceptable salt of dabigatran etexilate is dabigatran etexilate mesylate.

In an embodiment, the pharmaceutically acceptable surface-modified acidic medicinal auxiliary material or alkaline medicinal auxiliary material is treated with an aqueous solution of an alkaline substance for modification or an acidic substance for modification. Specifically, an aqueous solution of a pharmaceutically acceptable alkaline substance for modification or a pharmaceutically acceptable acidic substance for modification is formulated, and powder particles of the acidic medicinal auxiliary material or the alkaline medicinal auxiliary material are added to the aqueous solution of the alkaline substance for modification or the acidic substance for modification, to form a neutral salt layer on the surface of the powder particles of the acidic medicinal auxiliary material or the alkaline medicinal auxiliary material.

In an embodiment, the acidic medicinal auxiliary material is a pharmaceutically acceptable water-soluble acidic solid. In a preferred embodiment, the acidic medicinal auxiliary material is a pharmaceutically acceptable organic acid having a solubility of greater than 1% in water at 20° C. Further, the pH of 1% aqueous solution formulated with the acidic medicinal auxiliary material should be less than or equal to 5. In a preferred embodiment, the acidic medicinal auxiliary material includes, but is not limited to, one of pharmaceutically acceptable water-soluble organic acids such as tartaric acid, fumaric acid, succinic acid, citric acid, lactic acid and malic acid etc., or a hydrate or acidic salt thereof. In a preferred embodiment, the acidic medicinal auxiliary material also includes, but is not limited to, one of pharmaceutically acceptable water-soluble acidic amino acids such as glutamic acid and aspartic acid etc., or a hydrate or acidic salt thereof, or acidic salts of other pharmaceutically acceptable water-soluble amino acids such as acidic salts of glycine, alanine and serine etc. In a preferred embodiment, the acidic medicinal auxiliary material also includes, but is not limited to, one of acidic salts of pharmaceutically acceptable water-soluble acids such as inorganic dihydrogenphosphates and bisulfates etc., or a hydrate thereof.

In an embodiment, the alkaline medicinal auxiliary material is a pharmaceutically acceptable water-soluble alkaline solid. In a preferred embodiment, the alkaline medicinal auxiliary material is a pharmaceutically acceptable alkaline substance having a solubility of greater than 1% in water at 20° C. Further, the pH of 1% aqueous solution formulated with the alkaline medicinal auxiliary material should be greater than or equal to 9. In a preferred embodiment, the alkaline medicinal auxiliary material includes, but is not limited to, one of pharmaceutically acceptable water-soluble organic alkalis such as meglumine and trihydroxymethylaminomethane etc., or a hydrate thereof. In a preferred embodiment, the alkaline medicinal auxiliary material includes, but is not limited to, one of pharmaceutically acceptable water-soluble alkaline amino acids such as lysine, arginine, and histidine etc., or a hydrate or alkaline salt thereof, or alkaline salts of other pharmaceutically acceptable water-soluble amino acids such as alkaline salts of glycine, alanine and serine etc. In a preferred embodiment, the alkaline medicinal auxiliary material includes, but is not limited to, one of alkaline salts of pharmaceutically acceptable water-soluble inorganic acids such as alkaline carbonates and alkaline phosphates etc., or a hydrate thereof.

In an embodiment, the alkaline substance for modification is a pharmaceutically acceptable water-soluble alkaline solid or liquid. In a preferred embodiment, the alkaline substance for modification is a pharmaceutically acceptable alkaline substance having a solubility of greater than 1% in water at 20° C. Further, the pH of 1% aqueous solution formulated with the alkaline substance for modification should be greater than or equal to 9. In a preferred embodiment, the alkaline substance for modification includes, but is not limited to, one of pharmaceutically acceptable water-soluble inorganic alkaline substances such as hydroxide salts, water-soluble alkaline carbonates and water-soluble alkaline phosphates etc., or a hydrate thereof. In a preferred embodiment, the alkaline substance for modification includes, but is not limited to, one of pharmaceutically acceptable water-soluble organic alkaline substances such as aqueous ammonia, meglumine and trihydroxymethylaminomethane etc., or a hydrate thereof. In a preferred embodiment, the alkaline substance for modification includes, but is not limited to, one of alkaline salts of pharmaceutically acceptable water-soluble organic weak acids such as alkaline salts of acetic acid, tartaric acid, fumaric acid, succinic acid, citric acid, malic acid and lactic acid etc., or a hydrate thereof. In a preferred embodiment, the alkaline substance for modification includes, but is not limited to, one of some pharmaceutically acceptable alkaline amino acids such as lysine, arginine, and histidine etc., or a hydrate or alkaline salt thereof, or alkaline salts of other water-soluble amino acids such as alkaline salts of glycine, alanine and serine etc.

In an embodiment, the acidic substance for modification is a pharmaceutically acceptable water-soluble acidic solid or liquid. In a preferred embodiment, the acidic substance for modification is a pharmaceutically acceptable acidic substance having a solubility of greater than 1% in water at 20° C. Further, the pH of 1% aqueous solution formulated with the acidic substance for modification should be less than or equal to 5. In a preferred embodiment, the acidic substance for modification includes, but is not limited to, one of pharmaceutically acceptable water-soluble organic acids such as tartaric acid, fumaric acid, succinic acid, citric acid and malic acid etc., or a hydrate thereof. In a preferred embodiment, the acidic substance for modification includes, but is not limited to, one of pharmaceutically acceptable acidic amino acids such as glutamic acid and aspartic acid, or a hydrate or acidic salt thereof, or acidic salts of other water-soluble amino acids such as acidic salts of glycine, alanine and serine etc. In a preferred embodiment, the acidic substance for modification includes, but is not limited to, one of pharmaceutically acceptable water-soluble inorganic acids or acidic salts thereof such as hydrochloric acid, sulfuric acid, bisulfates, phosphoric acid, dihydrogenphosphates and bromic acid etc., or a hydrate thereof. In a preferred embodiment, the acidic substance for modification includes, but is not limited to, one of acidic salts of pharmaceutically acceptable water-soluble organic alkalis such as acidic salts of meglumine and trihydroxymethylaminomethane etc., or a hydrate thereof.

In an embodiment, the aqueous solution of the alkaline substance for modification or the acidic substance for modification has a concentration in the range of 1 wt % to a saturation concentration, preferably 5 to 40 wt %, more preferably 20 wt %. The saturation concentration of the aqueous solution of the alkaline substance for modification or the acidic substance for modification depends on the water solubility of the alkaline substance or acidic substance for surface modification.

In an embodiment, the powder particles of the acidic medicinal auxiliary material or the alkaline medicinal auxiliary material have a particle size of 0.4 to 1.5 mm, and pass through a 40 mesh to 60 mesh sieve.

In an embodiment, the pharmaceutical composition is loaded into hydroxypropylmethylcellulose capsules.

In an embodiment, the weight ratio of the added alkaline or acidic substance for modification to the acidic or alkaline medicinal auxiliary material solid to be modified is 0.1% to 10%, and the solid ratio is preferably 0.67% to 4%, more preferably 2%.

Pharmaceutically acceptable excipients which may be incorporated into the composition of the present invention include, but are not limited to, binders, disintegrants, diluents, surfactants, glidants, lubricants, etc., or combinations thereof.

Binders, disintegrants, diluents, surfactants, glidants, lubricants, etc., are exemplified below. It is necessary to disclose some pharmaceutically acceptable excipients herein, because some of the excipients are disclosed in the following examples.

The term "pharmaceutically acceptable salt" as used in the present invention refers to those salts which are suitable for use in contact with tissues of humans and other mammals without excessive toxicity, irritation, allergic reactions, etc., according to medical criteria. Such pharmaceutically acceptable salts are well known in the art.

In another aspect, the present invention also provides a process for preparing a pharmaceutical composition containing dabigatran etexilate or a pharmaceutically acceptable salt or hydrate thereof, comprising the step of mixing a pharmaceutically acceptable surface-modified acidic medicinal auxiliary material with dabigatran etexilate or a pharmaceutically acceptable salt or hydrate thereof, and optionally, at least one pharmaceutically acceptable excipients. Further, the pharmaceutically acceptable surface-modified acidic medicinal auxiliary material is prepared by the following process: according to the water solubility of the alkaline substance for modification, formulating an aqueous solution of the pharmaceutically acceptable alkaline substance for modification at a concentration of 1 wt % to the saturation concentration (preferably 5 to 40 wt %, more preferably 20 wt %); adding the acidic medicinal auxiliary material having a particle size of 0.4 to 1.5 mm, preferably 0.5 mm, to a certain volume of the above formulated aqueous solution of the pharmaceutically acceptable alkaline substance for modification; alkalizing the surface of powder particles of the acidic medicinal auxiliary material with the aqueous solution of the alkaline substance for modification, to form a neutral salt layer on the surface of the powder particles of the acidic medicinal auxiliary material. The acidic medicinal auxiliary material is a pharmaceutically acceptable organic acid having a solubility of greater than 1% in water at 20° C., and the organic acid as the acidic medicinal auxiliary material is one selected from the group consisting of tartaric acid, fumaric acid, succinic acid, citric acid, malic acid, glutamic acid and aspartic acid, or a hydrate or acidic salt thereof, preferably tartaric acid. The pharmaceutically acceptable alkaline substance for modification as used for alkalization is a pharmaceutically acceptable alkaline substance for modification, and the pharmaceutically acceptable alkaline substance for modification is one of sodium carbonate, potassium carbonate, sodium acetate, potassium acetate, sodium stearate, potassium stearate, lysine, arginine and histidine, or a hydrate thereof, preferably sodium carbonate. In addition to sodium carbonate, any weak-acid strong-alkali salts which are alkaline in an aqueous solution can be used in the present invention, without any particular limitation.

Specifically, the pharmaceutically acceptable surface-modified acidic medicinal auxiliary material may be prepared by the following process: first, formulating a sodium carbonate aqueous solution at a concentration of about 20% (by weight); with stirring, adding 10% of the above formulated sodium carbonate aqueous solution having a concentration of about 20% to tartaric acid powder particles having a particle size of 40 to 60 mesh; and after stirring, drying the tartaric acid powder particles in a drying apparatus such as a drying oven or a fluidized bed, to yield the modified tartaric acid powder particles.

The present invention has been made in view of the above-mentioned problems in the prior art, and an object of the present invention is to provide a method for surface modification of a medicinal auxiliary material, which has a simple process, achieves low production costs, and is applicable to the preparation of drugs which are liable to acids or alkalis in the formulation that however requires the use of acidic auxiliary materials or alkaline auxiliary materials therein.

To achieve the above object, the method for surface modification of a medicinal auxiliary material according to the present invention is characterized in that it comprises formulating an aqueous solution of a pharmaceutically acceptable alkaline substance for modification or a pharmaceutically acceptable acidic substance for modification; adding powder particles of an acidic medicinal auxiliary material or an alkaline medicinal auxiliary material to the aqueous solution of the alkaline substance for modification or the acidic substance for modification, to form a neutral salt layer on the surface of the powder particles of the acidic medicinal auxiliary material or the alkaline medicinal auxiliary material, wherein the acidic medicinal auxiliary material is a pharmaceutically acceptable organic acid having a water solubility of greater than 1 g/250 mL at 20° C., and the alkaline medicinal auxiliary material is a pharmaceutically acceptable alkaline substance having a water solubility of greater than 1 g/250 mL at 20° C.

Further, the pharmaceutically acceptable organic acid as the acidic medicinal auxiliary material is one of tartaric acid, fumaric acid, succinic acid, citric acid, malic acid, glutamic acid and aspartic acid, or a hydrate or acidic salt thereof.

Further, the pharmaceutically acceptable alkaline substance as the alkaline medicinal auxiliary material is one of lysine, arginine and histidine, or a hydrate thereof.

Further, the pharmaceutically acceptable alkaline substance for modification is one of sodium carbonate, potassium carbonate, sodium acetate, potassium acetate, sodium stearate, potassium stearate, lysine, arginine and histidine, or a hydrate thereof.

Further, the pharmaceutically acceptable acidic substance for modification is one of tartaric acid, fumaric acid, succinic acid, citric acid, malic acid, glutamic acid and aspartic acid, or a hydrate or acidic salt thereof, or one of sodium bisulfate, sodium dihydrogenphosphate and stearic acid, or a hydrate thereof.

Further, the aqueous solution of the alkaline substance for modification or the acidic substance for modification has a concentration of 5 to 40 wt %, and the concentration of the aqueous solution of the alkaline substance for modification or the acidic substance for modification depends on the water solubility of the alkaline substance or acidic substance for surface modification.

Further, the powder particles of the acidic medicinal auxiliary material or the alkaline medicinal auxiliary material have a particle size of 0.4 to 1.5 mm.

As described above, by chemically forming a neutral salt layer on the surface of the acidic medicinal auxiliary material or the alkaline medicinal auxiliary material, the pharmaceutical composition of the present invention separates the acidic medicinal auxiliary material or the alkaline medicinal auxiliary material from the active drug ingredient which is labile to acids or alkalis in the formulation that however requires the use of acidic auxiliary materials or alkaline auxiliary materials therein, thereby improving the storage stability of the drug. Furthermore, this method utilizes only an one-step reaction to modify the surface of the acidic medicinal auxiliary material or the alkaline medicinal auxiliary material, and thus has simple operations and achieves low production costs. The method for surface modification of a medicinal auxiliary material according to the present invention performs the modification of the surface of the acidic medicinal auxiliary material or the alkaline medicinal auxiliary material by only an one-step reaction, and thus has a simple process and achieves low production costs.

By chemically forming a neutral salt layer on the surface of the acidic medicinal auxiliary material or the alkaline medicinal auxiliary material, the present invention separates the acidic medicinal auxiliary material or the alkaline medicinal auxiliary material from the active drug ingredient which is labile to acids or alkalis in the formulation that however requires the use of acidic medicinal auxiliary materials or alkaline medicinal auxiliary materials therein, thereby improving the storage stability of the drug.

The pharmaceutical composition containing dabigatran etexilate prepared as described above is useful for the following clinical indications: 1) for preventing deep venous thrombosis and pulmonary embolism after artificial (knee or hip) arthroplasty, in which case an anticoagulant drug is conventionally used after the surgery; 2) for preventing stroke and thrombosis in a patient with abnormal heart rhythm (atrial fibrillation).

DESCRIPTION OF EMBODIMENTS

To clearly illustrate the object, the technical solution and the advantages of the present invention, the specific embodiments of the present invention will be described below in detail, with reference to the accompanying drawings.

The technical solutions in the examples of the present invention will be described below in detail, with reference to the examples of the present invention. Obviously, the examples described herein are merely a part of the examples of the present invention, and do not represent all. On the basis of the examples shown in the present invention, all the other examples which can be obtained by those of ordinary skill in the art without paying any creative efforts are within the scope of the present invention.

It should be noted that in this context, the terms "comprise", "include", and "contain" or any other variants thereof are intended to be nonexclusive, so that a process, method, article or apparatus comprising a series of elements includes not only those elements, but also other elements which are not explicitly listed, or elements which are inherent to such a process, method, article, or apparatus. Meanwhile, in the present invention, the dissolution is tested at 100 rpm and at a temperature of 37° C. by the basket method specified in the Pharmacopoeia, and water is used as the solvent.

Figure 1:
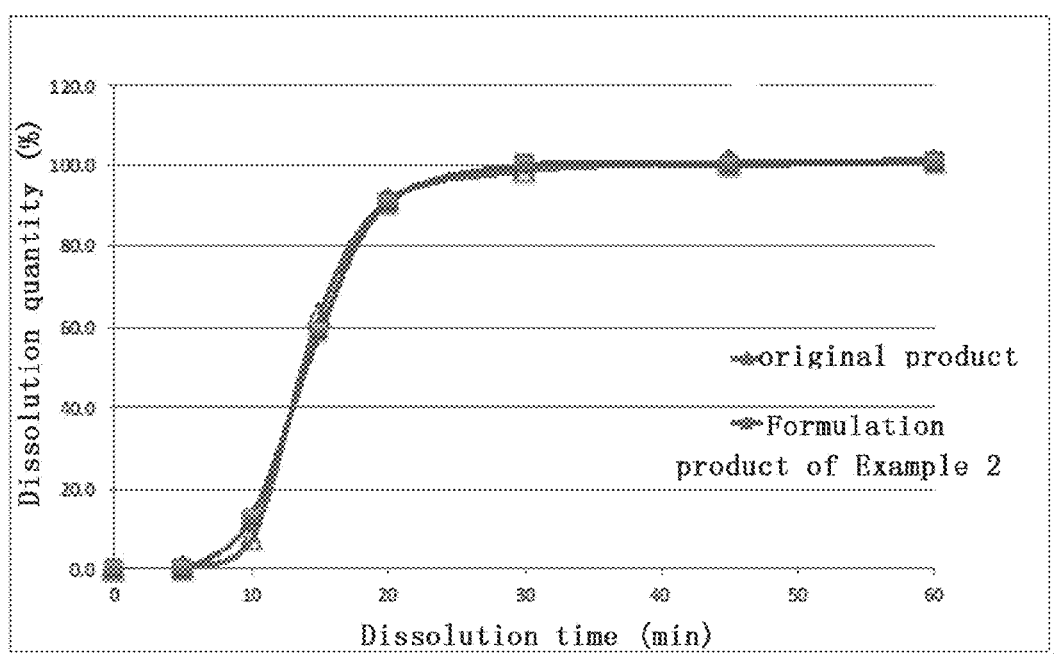
FIG. 1 shows that the drug obtained in Example 2 achieves the same dissolution effect as the prior art product.
Figure 2:
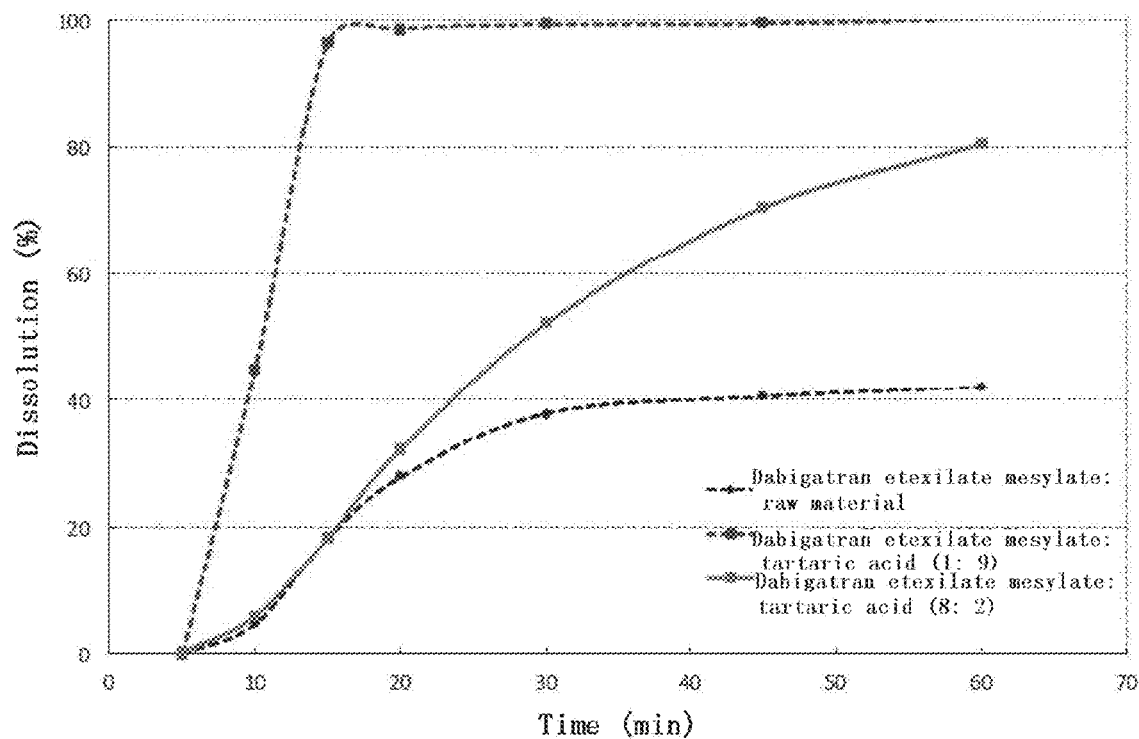
FIG. 2 shows the dissolution results of the capsules of Example 3 which were prepared with the raw material dabigatran etexilate mesylate and the modified tartaric acid in different proportions.

FIG. 1 shows that the drug obtained according to Formula 2 achieves the same dissolution effect as the prior art product. FIG. 2 shows the dissolution results of the capsules prepared with the raw material dabigatran etexilate mesylate and the modified tartaric acid in different proportions.

The method for surface modification of an acidic medicinal auxiliary material according to the present invention comprises: according to the water solubility of the alkaline substance for modification, formulating an aqueous solution of the pharmaceutically acceptable alkaline substance for modification at a concentration of 5 to 40 wt %; adding the acidic medicinal auxiliary material having a particle size of 0.4 to 1.5 mm, preferably 0.5 mm, to a certain volume of the above formulated aqueous solution of the pharmaceutically acceptable alkaline substance for modification having a concentration of 5 to 40 wt %; alkalizing the surface of powder particles of the acidic medicinal auxiliary material with the above aqueous solution of the alkaline substance for modification, to form a neutral salt layer on the surface of the powder particles of the acidic medicinal auxiliary material. The acidic medicinal auxiliary material is a pharmaceutically acceptable organic acid having a water solubility of greater than 1 g/250 mL at 20° C., and the organic acid as the acidic medicinal auxiliary material is one selected from the group consisting of tartaric acid, fumaric acid, succinic acid, citric acid, malic acid, glutamic acid and aspartic acid, or a hydrate or acidic salt thereof, preferably tartaric acid. The pharmaceutically acceptable alkaline substance for modification as used for alkalization is a pharmaceutically acceptable alkaline substance for modification, and the pharmaceutically acceptable alkaline substance for modification is one of sodium carbonate, potassium carbonate, sodium acetate, potassium acetate, sodium stearate, potassium stearate, lysine, arginine and histidine, or a hydrate thereof, preferably sodium carbonate.

First, a sodium carbonate aqueous solution having a concentration of 20% (by weight) is formulated; with stirring, 10% of the above formulated sodium carbonate aqueous solution having a formulation concentration of 20% is added to tartaric acid powder particles having a particle size of 0.4 to 1.5 mm, preferably 0.5 mm; and after stirring, the tartaric acid powder particles are dried in a drying apparatus such as a drying oven or a fluidized bed, to yield the modified tartaric acid powder particles.

Since the sodium carbonate aqueous solution is alkaline, a chemical reaction will occur between the alkaline sodium carbonate and the acidic tartaric acid, forming a neutral salt layer on the surface of the tartaric acid powder particles. The neutral salt layer separates the acidic medicinal auxiliary material tartaric acid from the active drug ingredient which is labile to acids in the formulation that however requires the use of acidic auxiliary materials therein, thereby improving the storage stability of the drug. In addition to sodium carbonate, any weak-acid strong-alkali salts which are alkaline in an aqueous solution can be used in the present invention, without any particular limitation.

Example 1

Formula 1

| | |
|---|---|
| Dabigatran etexilate mesylate | 173.0 mg |
| Tartaric acid | 173.5 mg |
| Sodium carbonate | 3.54 mg |
| Total | 350 mg |
| Control formula: | |
| Dabigatran etexilate mesylate | 173.0 mg |
| Tartaric acid | 177 mg |
| Total | 350 mg |

Dabigatran etexilate mesylate, tartaric acid, and sodium carbonate are all commercially available raw materials.

According to Formula 1, a quantified amount of sodium carbonate was dissolved in 20 mL water; with stirring, tartaric acid powder particles having a particle size of 0.4 to 1.5 mm were added to the sodium carbonate aqueous solution; and after stirring, the tartaric acid powder particles were dried in a drying apparatus such as a drying oven or a fluidized bed, to yield the modified tartaric acid powder particles.

The modified tartaric acid powder particles were thoroughly mixed with dabigatran etexilate mesylate indicated in Formula 1 and loaded into hydroxypropylmethylcellulose (HPMC) capsules. The capsules were then packed into high density polyethylene (HDPE) bottles containing a desiccant. After being stored at 75° C. and 75% RH for 1 week and 2 weeks, capsule samples were tested by HPLC and the results are shown in the following table.

According to the control formula, tartaric acid powder particles were thoroughly mixed with dabigatran etexilate mesylate indicated in the control formula and loaded into hydroxypropylmethylcellulose (HPMC) capsules. The capsules were then packed into high density polyethylene (HDPE) bottles containing a desiccant. After being stored at 75° C. and 75% RH for 1 week and 2 weeks, capsule samples were tested by HPLC and the results are shown in the following table.

TABLE 1

| | Total amount of decomposition products (%) | |
|---|---|---|
| Storage duration | Formula 1 | Control formula |
| 0 day | 0.27 | 0.31 |
| 1 week | 2.9 | 3.6 |
| 2 weeks | 4.8 | 10.9 |

As can be seen from the above results, the formulation into which the modified tartaric acid was added exhibits a greatly improved storage stability. As shown in Table 1, it can be seen that as the storage duration changes, the stability is 200% or more relative to the unmodified control.

Example 2

Formula 2

| | |
|---|---|
| Dabigatran etexilate mesylate | 173.0 mg |
| Tartaric acid | 166.6 mg |
| Sodium carbonate | 3.4 mg |
| HPC | 10.0 mg |
| Silica powder | 8.0 mg |
| SDS | 5.0 mg |
| Lactose | 45.0 mg |
| Magnesium stearate | 6.0 mg |
| Total | 420.0 mg |

According to Formula 2, a quantified amount of sodium carbonate was dissolved in 20 mL water; with stirring, tartaric acid powder particles having a particle size of 0.4 to 1.5 mm were added to the sodium carbonate aqueous solution; and after stirring, the tartaric acid powder particles were dried in a drying apparatus such as a drying oven or a fluidized bed, to yield the modified tartaric acid powder particles.

Then, dabigatran etexilate mesylate were mixed with the modified tartaric acid powder particles, followed by other pharmaceutically acceptable excipients, and loaded into HPMC capsules to yield the pharmaceutical formulation product.

Example 3

Dabigatran etexilate mesylate were mixed with the modified tartaric acid powder particles, followed by other pharmaceutically acceptable excipients, and loaded into HPMC capsules to yield the pharmaceutical formulation product. FIG. 2 shows the dissolution results of the capsules prepared with the raw material dabigatran etexilate mesylate and the modified tartaric acid in different proportions. The dissolution was tested at 100 rpm and at a temperature of 37° C. by the basket method specified in the Pharmacopoeia, and water was used as the solvent.

The results show that the dissolution of the dabigatran etexilate mesylate formulation product into which the modified tartaric acid was added is significantly improved as compared with the dissolution of the formulation into which the modified tartaric acid was not added.

To sum up, the pharmaceutical composition of the present invention exhibits a superior storage stability, achieves a high solubility, and provides the desired bioavailability. Meanwhile, the method for surface modification of a medicinal auxiliary material performs the modification of the surface of the acidic medicinal auxiliary material by only an one-step reaction, and thus has a simple process and achieves low production costs.

The specific embodiments described above are merely illustrative of the spirit of the present invention, and the scope of the present invention is not limited thereto. It will be apparent to those skilled in the art that, other embodiments can be readily made by way of modifications, replacements or variations according to the technical contents disclosed in the present Description, and all of the other embodiments are intended to be within the scope of the present invention.

What is claimed is:

1. A solid oral pharmaceutical composition, comprising:
    (i) a first component, wherein the first component comprises an active pharmaceutical ingredient or a pharmaceutically acceptable salt or hydrate thereof, wherein the active pharmaceutical ingredient or the pharmaceutically acceptable salt or hydrate thereof is labile to acids or alkalis in the pharmaceutical composition and is substantially insoluble in physiological conditions;
    (ii) a second component, wherein the second component comprises:
        (a) a pharmaceutically acceptable surface-modified acidic auxiliary material, wherein the surface of the pharmaceutically acceptable surface-modified acidic auxiliary material comprises a neutral salt layer that comprises: 1) an anion of an acidic medicinal auxiliary material in a powdered form; and 2) a cation of a pharmaceutically acceptable alkaline substance for surface modification, and wherein a weight ratio of the pharmaceutically acceptable alkaline substance for surface modification to the acidic medicinal auxiliary material is 0.1% to 10%; or
        (b) a pharmaceutically acceptable surface-modified alkaline auxiliary material, wherein the surface of the pharmaceutically acceptable surface-modified alkaline auxiliary material comprises a neutral salt layer that comprises: 1) a cation of an alkaline medicinal auxiliary material in a powdered form; and 2) an anion of a pharmaceutically acceptable acidic substance for surface modification, and wherein a weight ratio of the pharmaceutically acceptable acidic substance for surface modification to the alkaline medicinal auxiliary material is 0.1% to 10%; and
wherein the pharmaceutical composition is in a solid dosage form.

2. The solid oral pharmaceutical composition of claim 1, wherein the weight ratio of the pharmaceutically acceptable alkaline substance for surface modification to the acidic medicinal auxiliary material is 0.67% to 4%; or wherein the weight ratio of the pharmaceutically acceptable acidic substance for surface modification to the alkaline medicinal auxiliary material is 0.67% to 4%.

3. The solid oral pharmaceutical composition of claim 1, wherein the acidic medicinal auxiliary material is a pharmaceutically acceptable organic acid having a water solubility of greater than 1 g/250 mL at 20° C.; or wherein the alkaline medicinal auxiliary material is a pharmaceutically acceptable alkaline substance having a water solubility of greater than 1 g/250 mL at 20° C.

4. The solid oral pharmaceutical composition of claim 1, wherein the acidic medicinal auxiliary material is selected from the group consisting of tartaric acid, fumaric acid, succinic acid, citric acid, malic acid, glutamic acid, aspartic acid, a hydrate thereof, and an acidic salt; and wherein the pharmaceutically acceptable alkaline substance for surface modification is selected from the group consisting of aqueous ammonia, meglumine, trihydroxymethylaminomethane, sodium carbonate, potassium carbonate, sodium acetate, potassium acetate, sodium stearate, potassium stearate, lysine, arginine and histidine, and a hydrate thereof.

5. The solid oral pharmaceutical composition of claim 1, wherein the alkaline medicinal auxiliary material is selected from the group consisting of lysine, arginine and histidine, and a hydrate thereof; and wherein the pharmaceutically acceptable acidic substance for surface modification is selected from the group consisting of tartaric acid, fumaric acid, succinic acid, citric acid, malic acid, glutamic acid, aspartic acid, a hydrate thereof, and an acidic salt.

6. The solid oral pharmaceutical composition of claim 1, wherein the pharmaceutically acceptable alkaline substance for surface modification is selected from the group consisting of sodium carbonate, potassium carbonate, sodium acetate, potassium acetate, lysine, arginine and a hydrate thereof.

7. The solid oral pharmaceutical composition of claim 1, wherein the acidic medicinal auxiliary material or the alkaline medicinal auxiliary material has a particle size of 0.4 to 1.5 mm.

8. The solid oral pharmaceutical composition of claim 1, wherein the acidic medicinal auxiliary material is a pharmaceutically acceptable organic acid, and wherein the pharmaceutically acceptable alkaline substance is a carbonate base.

9. The solid oral pharmaceutical composition of claim 8, wherein the pharmaceutically acceptable organic acid is tartaric acid, and wherein the carbonate base is sodium carbonate.

10. A solid oral pharmaceutical composition, comprising:
    (i) a first component, wherein the first component comprises an active pharmaceutical ingredient or a pharmaceutically acceptable salt or hydrate thereof, wherein the active pharmaceutical ingredient or the pharmaceutically acceptable salt or hydrate thereof is labile to acids or alkalis in the pharmaceutical composition and is substantially insoluble in physiological conditions;
    (ii) a second component, wherein the second component comprises:
        (a) a pharmaceutically acceptable surface-modified acidic auxiliary material, wherein the surface of the pharmaceutically acceptable surface-modified acidic auxiliary material comprises a neutral salt layer formed by reacting: 1) a powdered form of an acidic medicinal auxiliary material; and 2) an aqueous solution comprising a pharmaceutically acceptable alkaline substance for surface modification, wherein the acidic medicinal auxiliary material is selected from the group consisting of tartaric acid, fumaric acid, succinic acid, citric acid, malic acid, glutamic acid, aspartic acid, a hydrate thereof, and an acidic salt thereof, and wherein the pharmaceutically acceptable alkaline substance for surface modification is selected from the group consisting of aqueous ammonia, meglumine, trihydroxymethylaminomethane, sodium carbonate, potassium carbonate, sodium acetate, potassium acetate, sodium stearate, potassium stearate, lysine, arginine and histidine, and a hydrate thereof, and wherein a weight ratio of the pharmaceutically acceptable alkaline substance for surface modification to the acidic medicinal auxiliary material is 0.1% to 10%; or (b) a pharmaceutically acceptable surface-modified alkaline auxiliary material, wherein the surface of the pharmaceutically acceptable surface-modified alkaline auxiliary material comprises a neutral salt layer formed by reacting: 1) a powdered form of an alkaline medicinal auxiliary material; and 2) an aqueous solution comprising a pharmaceutically acceptable acidic substance for surface modification, wherein the alkaline medicinal auxiliary material is selected from the group consisting of lysine, arginine, histidine, and a hydrate thereof, and wherein the pharmaceutically acceptable acidic substance for surface modification is selected from the group consisting of tartaric acid, fumaric acid, succinic acid, citric acid, malic acid, glutamic acid, aspartic acid, a hydrate thereof, and an acidic salt, and wherein a weight ratio of the pharmaceutically acceptable acidic substance for surface modification to the alkaline medicinal auxiliary material is 0.1% to 10%; and wherein the pharmaceutical composition is in a solid dosage form.

11. The solid oral pharmaceutical composition of claim 10, wherein the weight ratio of the pharmaceutically acceptable alkaline substance for surface modification to the acidic medicinal auxiliary material is 0.67% to 4%; or the weight ratio of the pharmaceutically acceptable acidic substance for surface modification to the alkaline medicinal auxiliary material is 0.67% to 4%.

12. The solid oral pharmaceutical composition of claim 10, wherein the acidic medicinal auxiliary material or the alkaline medicinal auxiliary material has a particle size of 0.4 to 1.5 mm.

13. The solid oral pharmaceutical composition of claim 10, wherein the acidic medicinal auxiliary material is a pharmaceutically acceptable organic acid having a water solubility of greater than 1 g/250 mL at 20° C., or wherein the alkaline medicinal auxiliary material is a pharmaceutically acceptable alkaline substance having a water solubility of greater than 1 g/250 mL at 20° C.

14. The solid oral pharmaceutical composition of claim 10, wherein the acidic medicinal auxiliary material is tartaric acid, and wherein the pharmaceutically acceptable alkaline substance for surface modification is sodium carbonate.

15. The solid oral pharmaceutical composition of claim 1, wherein the active pharmaceutical ingredient or the pharmaceutically acceptable salt or hydrate thereof is labile to acids in the pharmaceutical composition, and wherein the second component comprises (a) the pharmaceutically acceptable surface-modified acidic auxiliary material.

16. The solid oral pharmaceutical composition of claim 1, wherein the active pharmaceutical ingredient or the pharmaceutically acceptable salt or hydrate thereof is labile to alkalis in the pharmaceutical composition, and wherein the second component comprises (b) the pharmaceutically acceptable surface-modified alkaline auxiliary material.

17. The solid oral pharmaceutical composition of claim 1, wherein the pharmaceutical composition further comprises a pharmaceutically acceptable excipient, and wherein the pharmaceutically acceptable excipient comprises binders, disintegrants, diluents, surfactants, glidants, lubricants, or combinations thereof.

18. The solid oral pharmaceutical composition of claim 10, wherein the active pharmaceutical ingredient or the pharmaceutically acceptable salt or hydrate thereof is labile to acids in the pharmaceutical composition, and wherein the second component comprises (a) the pharmaceutically acceptable surface-modified acidic auxiliary material.

19. The solid oral pharmaceutical composition of claim 10, wherein the active pharmaceutical ingredient or the pharmaceutically acceptable salt or hydrate thereof is labile to alkalis in the pharmaceutical composition, and wherein the second component comprises (b) the pharmaceutically acceptable surface-modified alkaline auxiliary material.

20. The solid oral pharmaceutical composition of claim 10, wherein the pharmaceutical composition further comprises a pharmaceutically acceptable excipient, and wherein the pharmaceutically acceptable excipient comprises binders, disintegrants, diluents, surfactants, glidants, lubricants, or combinations thereof.

21. The solid oral pharmaceutical composition of claim 10, wherein the aqueous solution comprising the pharmaceutically acceptable alkaline substance for surface modification has a concentration of 5 to 40 wt %; or wherein the aqueous solution comprising the pharmaceutically acceptable acidic substance for surface modification has a concentration of 5 to 40 wt %.

* * * * *

UNITED STATES PATENT AND TRADEMARK OFFICE
CERTIFICATE OF CORRECTION

| | | |
|---|---|---|
| PATENT NO. | : 12,133,847 B2 | Page 1 of 1 |
| APPLICATION NO. | : 17/369531 | |
| DATED | : November 5, 2024 | |
| INVENTOR(S) | : Wang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 341 days.

Signed and Sealed this
Thirtieth Day of September, 2025

John A. Squires
*Director of the United States Patent and Trademark Office*